(12) United States Patent
Song et al.

(10) Patent No.: US 12,114,868 B2
(45) Date of Patent: Oct. 15, 2024

(54) NONDESTRUCTIVE AUTOGRAFT EXTRACTING DEVICE FOR AUTOLOGOUS OSTEOCHONDRAL TRANSPLANTATION

(71) Applicant: UNIVERSITY OF CENTRAL FLORIDA RESEARCH FOUNDATION, INC., Orlando, FL (US)

(72) Inventors: Sang-Eun Song, Orlando, FL (US); Pradipta Biswas, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 107 days.

(21) Appl. No.: 17/929,873

(22) Filed: Sep. 6, 2022

(65) Prior Publication Data

US 2023/0074037 A1    Mar. 9, 2023

Related U.S. Application Data

(62) Division of application No. 16/536,134, filed on Aug. 8, 2019, now Pat. No. 11,432,825.

(60) Provisional application No. 62/716,114, filed on Aug. 8, 2018.

(51) Int. Cl.
| | | |
|---|---|---|
| *A61B 17/14* | (2006.01) | |
| *A61B 17/32* | (2006.01) | |
| *A61B 34/30* | (2016.01) | |
| *A61F 2/28* | (2006.01) | |
| *A61F 2/46* | (2006.01) | |

(52) U.S. Cl.
CPC ...... *A61B 17/142* (2016.11); *A61B 17/32002* (2013.01); *A61B 34/30* (2016.02); *A61F 2/28* (2013.01); *A61F 2/4601* (2013.01); *A61F 2/4644* (2013.01); *A61B 2017/320032* (2013.01); *A61F 2002/4645* (2013.01); *A61F 2002/4649* (2013.01)

(58) Field of Classification Search
CPC . A61B 17/142; A61B 17/32002; A61B 17/14; A61B 17/149; A61F 2002/4645; A61F 2002/4649
See application file for complete search history.

(56) References Cited

U.S. PATENT DOCUMENTS

| | | |
|---|---|---|
| 9,351,741 B2 | 5/2016 | Schmitz et al. |
| 11,432,825 B2 | 9/2022 | Song et al. |
| 2009/0062802 A1 | 3/2009 | Palmer et al. |

OTHER PUBLICATIONS

Biswas, P. et al., "A Robotic Nondestructive Osteochondral Tissue Harvesting for Autograft Transplantation" EPiC Series in Health Sciences, 2019, CAOS2019.The19th Annual Meeting of the International Society for Computer Assisted Orthopaedic Surgery, 4 pages.

(Continued)

*Primary Examiner* — Julian W Woo
(74) *Attorney, Agent, or Firm* — Timothy H. Van Dyke; Wolter, Van Dyke, Davis, PLLC

(57) ABSTRACT

Systems and methods are disclosed for harvesting tissue from a donor site. Exemplary embodiments include a first and second conduit through which a flexible saw component is guided. Certain embodiments include a mechanism which facilitates insertion of the flexible cutting member component parallel to the transverse plane and slicing the graft parallel to the coronal plane to extract the graft.

12 Claims, 8 Drawing Sheets

(56) References Cited

OTHER PUBLICATIONS

Biswas, P. et al., "A Method and Mechanism for Harvesting Intact Autograft for Osteochondral Transplantation", Proceedings of the 2019 Design of Medical Devices Conference, DMD2019-3260, 5 pages.

Biswas, P. et al., "A Nondestructive Autograft Extraction Method for Autologous Osteochondral Transplantation", 31st Florida Conference on Recent Advances in Robotics May 10-11, 2018, 4 pages.

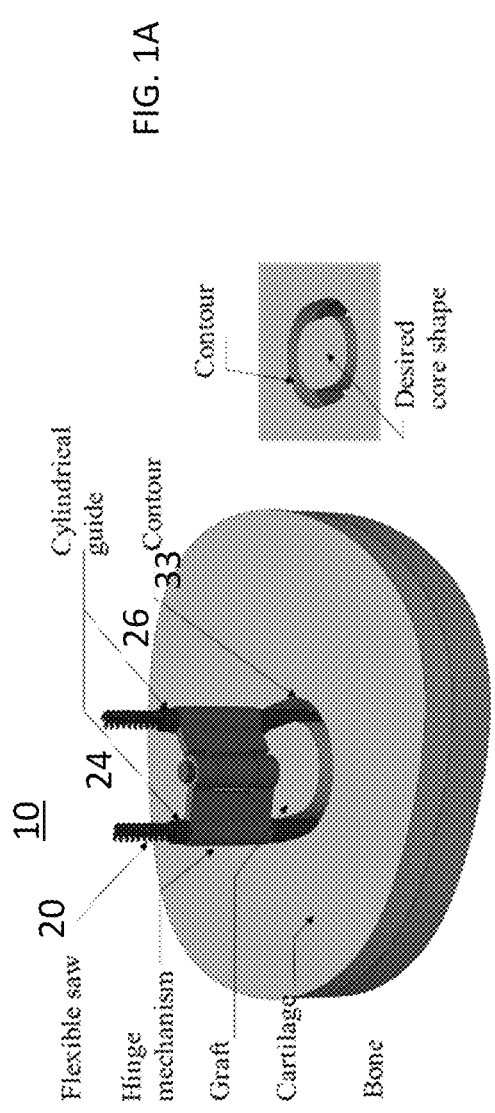
FIG. 1A
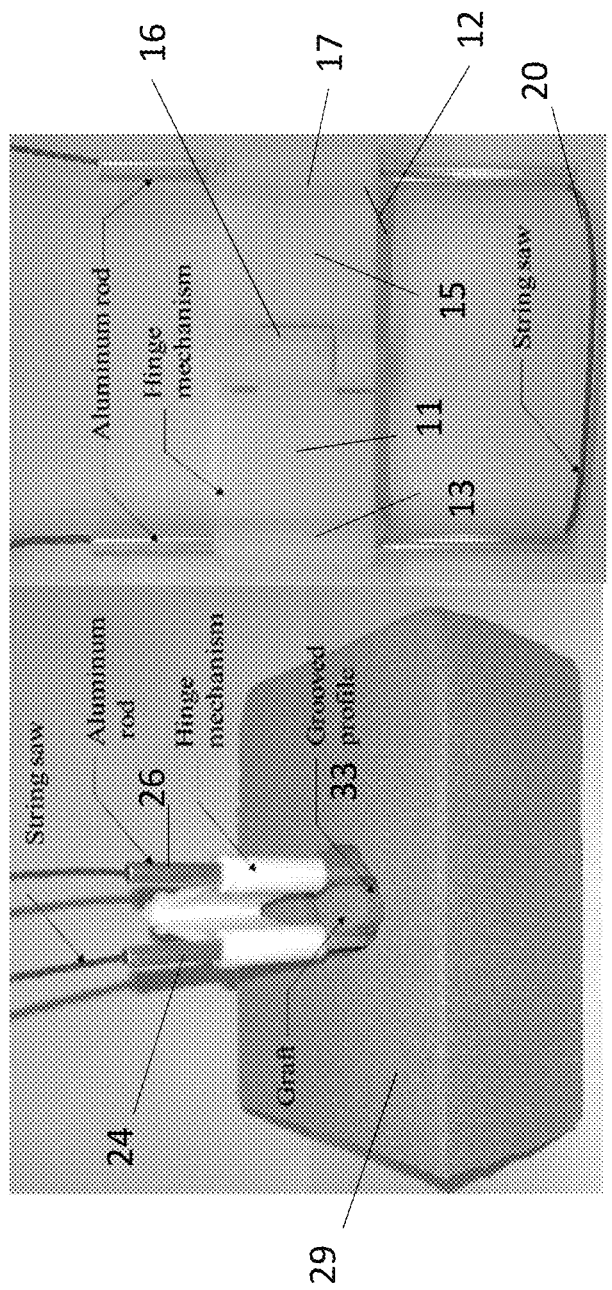
FIG. 2A
FIG. 2B

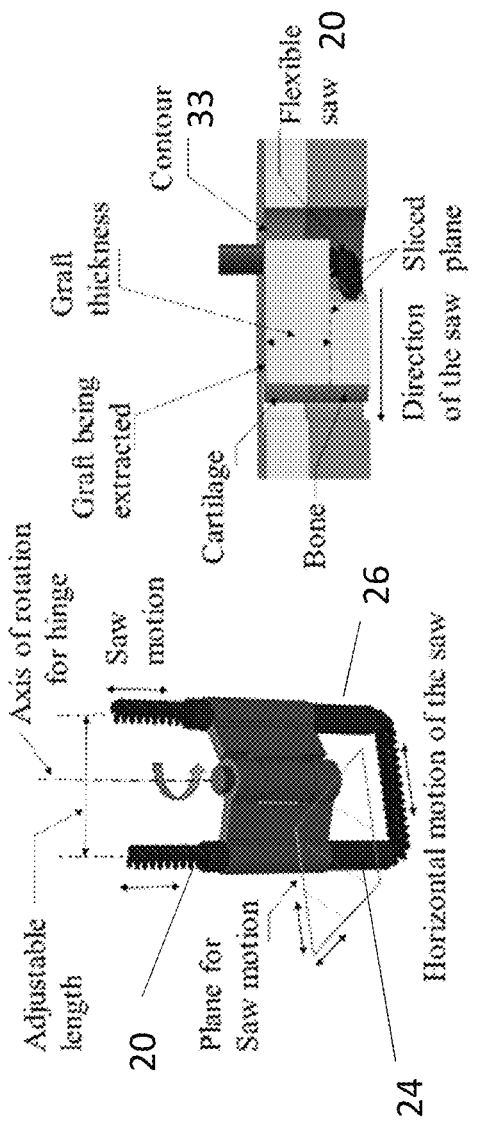

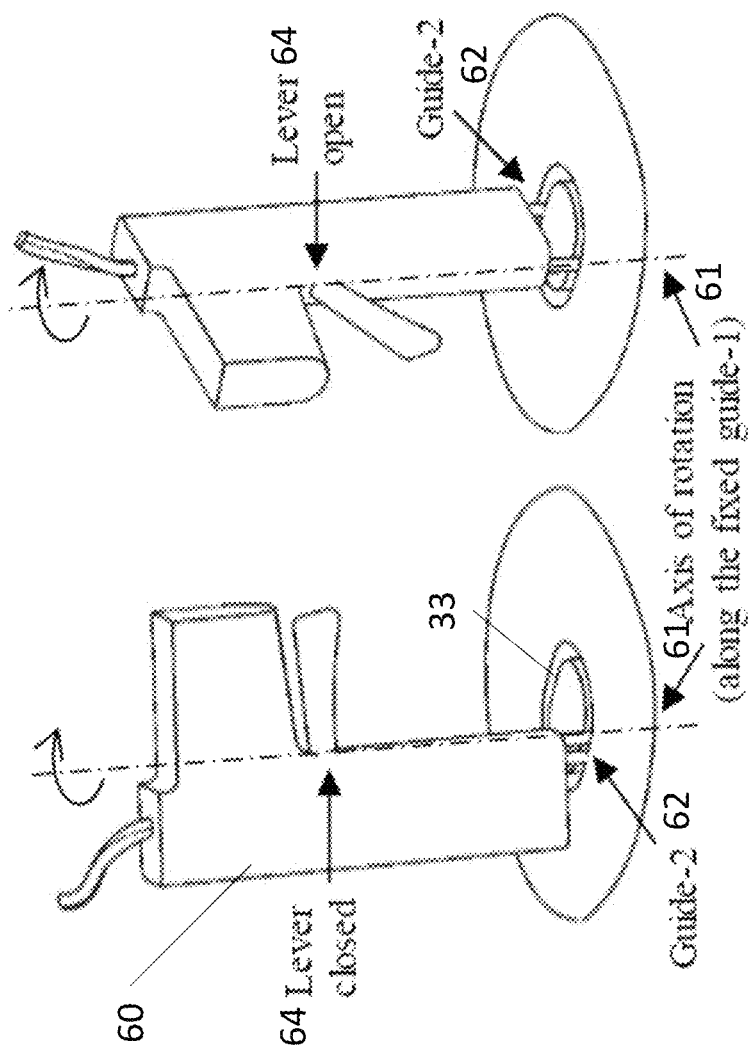

NONDESTRUCTIVE AUTOGRAFT EXTRACTING DEVICE FOR AUTOLOGOUS OSTEOCHONDRAL TRANSPLANTATION

BACKGROUND

Osteoarthritis (OA) is the degeneration of articular cartilage and subchondral bone, often leading to pain, joint stiffness, and disability. Post Traumatic Osteoarthritis (PTOA) develops after a joint injury. Nearly 27 million adults aged 25 or above have a clinical diagnosis of OA. Among those PTOA affects 5.6 million people and is the cause of about 12% of osteoarthritis of the hip, knee, and ankle in the United States. When osteoarthritis progresses to the point that conservative measures are no longer effective, then surgical treatments are often performed. Surgical treatment may include debriding, reconstructing, or replacing the worn out joint surfaces. There are numerous surgical procedures aimed to repair or regenerate osteoarthritic lesions which include microfracture, autologous osteochondral cylinder transplantation (mosaicplasty), artificial bone graft substitutes and cell-based repair techniques, such as autologous chondrocyte implantation (ACT). Compared to mosaicplasty, ACT is more expensive, requires two procedures and an open arthrotomy. The microfracture technique is typically used for small defect areas while osteochondral transplantation is used for larger cartilage defects and has advantages over microfracture.

For osteochondral transplantation, plugs of healthy cartilage with subchondral bone are extracted either from the joints of a cadaver (allografts) or from a non-load bearing area of the patient (autografting) and inserted into the arthritic defect (in case of mosaicplasty) shown in FIGS. 3 (a) and (b). Unlike allografts, osteochondral autograft transplantation (OAT) uses the patient's own tissue eliminating any risk of infectious disease transmission. Both cartilage and bone are harvested from the donor site, so OAT has the advantage of filling osteochondral defects, making OAT an option in treating smaller osteochondritis dissecans lesions.

For mosaicplasty, combination of grafts are able to resurface 80-100 of the damaged area. Although, mosaicplasty is a well-established technique for cartilage repair, due to current technological limitations, harvesting large grafts is not practical. The success of harnessing a larger and complex shaped graft to replace the damaged osteochondral area lies in effective extraction of the cartilage-bone graft from the donor site. Currently, no method exists to perform this procedure.

BRIEF DESCRIPTION OF DRAWINGS

FIG. 1(A) represents a CAD model of a donor tissue removal setup.

FIG. 1(B) is a diagram showing a flexible string saw (Gigli saw) mechanism,

FIG. 1(C) is a cross-section diagram of donor tissue while being sliced.

FIG. 2(A) is a photograph showing a foam removal experiment using an apparatus embodiment.

FIG. 2(B) showing a photograph of an apparatus embodiment.

FIG. 8 shows a diagram demonstrating operation of the system shown in FIG. 6.

DETAILED DESCRIPTION

Figure 3B:
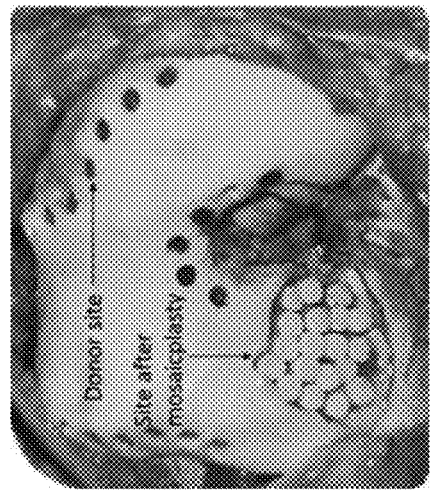
FIG. 3(B) site after mosaicplasty.
Figure 3A:
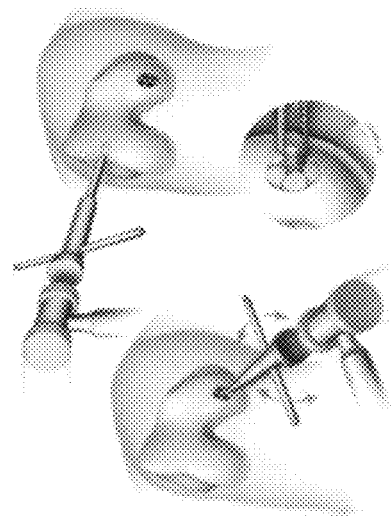
FIG. 3(A) Steps in mosaicplasty.
Figures 4A, 4B:
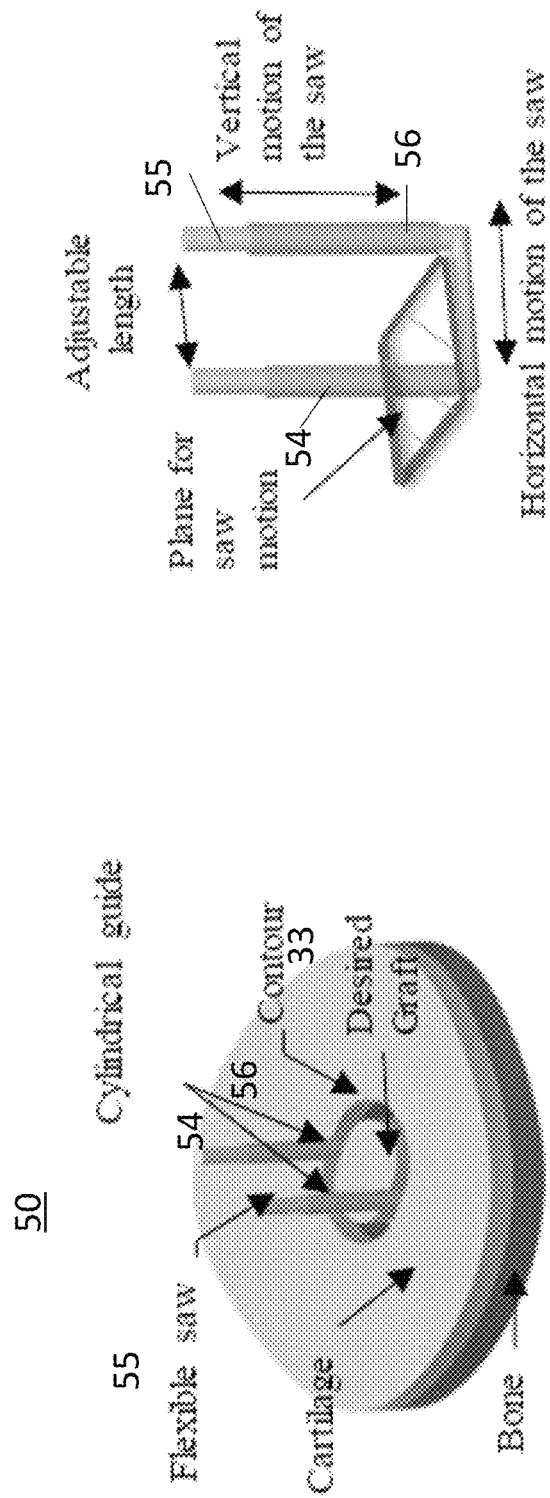
FIG. 4(A): provides a diagram showing two conduits inserted in the contour along with the flexible saw for graft harvesting, FIG. 4(B) provides a diagram showing conversion of the flexible saw motion to the cutting plane.

Harvesting large cartilage/bone grafts intact is not possible simply because the deep side cannot be cut. The difficulty in extracting donor grafts for autografting lies in separating the bottom surface of the graft from the donor site. Accordingly, systems, devices and methods are described herein that enable the procurement of larger cartilage/bone grafts that achieve separation of the graft bottom surface from the donor site.

According to one embodiment, disclosed is a unique bone cutting system that allows for drilling/milling a profile around a region of interest from a non-weight bearing site according to the damaged cartilage profile and slicing off the bottom part of the graft from the bone. The system includes a flexible cutting member (e.g. saw component) and a mechanism which facilitates insertion of the flexible cutting member component parallel to the transverse plane and slicing the graft parallel to the coronal plane to extract the graft.

According to a specific embodiment, disclosed is a cutting apparatus for cutting tissue (e.g. bone) that includes a base having a first end and a second end, and a hinge disposed on said base between said first and second ends. The hinge allows the base to pivot at the hinge to move the first and second ends nearer each other. The apparatus also includes a first conduit and a second conduit associated with the first end and second end, respectively. The first and second conduits have a distal end and proximal end. The apparatus also includes a cutting member disposed within the first and second conduits, said cutting member spans between the distal end of the first conduit and distal end of second conduit. Typically, the cutting member is a flexible saw component, similar to commercially available Gigli saws used in amputations but preferably adapted to be more flexible to handle the sharp bends into the first and second conduits. In a specific version, the base has a first and second channel disposed at said first end and second end, respectively, and the first and second conduits are held within said channel. The conduits may be made of any suitable rigid materials, such as metal, wood, plastics and the like.

Another disclosed embodiment pertains to a method for cutting tissue involving an apparatus or system as described herein. The apparatus is inserted into a groove (contour) defined or created in the tissue; and a reciprocating motion of the cutting member is conducted to facilitate cutting the tissue. Typically, the tissue is cut in a plane transverse to the plane of the contour. It is important to have the two conduits parallel to each other and perpendicular to the coronal plane (i.e., the slicing plane) to follow the contour properly and extract a graft with a flat sliced surface. Certain embodiments described herein achieve such cutting profile.

In a further embodiment, disclosed is a system comprising a robotic arm; a harness device associated with the robotic arm; a first conduit and a second conduit movably associated with the harness device such that the harness device moves or allows movement of the first and second conduits toward or away from each other; and a saw component extending within the first and second conduits and associated with the harness device such that the harness device provides motion to the saw component to induce a cutting effect between distal ends of the first and second conduits.

In yet a further embodiment, provided is a system comprising a harness device; a fixed conduit and a movable conduit associated with the harness device such that a distance between the fixed conduit and movable conduit may be increased or decreased by movement of the movable conduit; a lever that controls the distance between the fixed conduit and movable conduit; and a saw component extending within the fixed conduit and movable conduit and associated with the harness device such that the harness device provides motion to the saw component to induce a cutting effect between distal ends of the fixed and movable conduits.

Details of exemplary embodiments are provided below and in the referenced figures.

Definitions

As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another. The modifier "about" used in connection with a quantity is inclusive of the stated value and has the meaning dictated by the context. It is to be noted that all ranges disclosed within this specification are inclusive and are independently combinable.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7. As another non-limiting example, a range of "between 20 and 10" can also include the values 20, 10.

Description of Illustrated Embodiments

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

Turning to FIG. 1A and FIG. 2B shown is a cutting system 10 that is useful for procuring grafts from a donor site. The system 10 includes a base 12 that includes a first arm 11 having a first end 13 and a second arm 15 having a second end 17 and a hinge 16 disposed between the two ends 13 and 17 that pivotally associates the first and second arms 11, 15. As the hinge 16 pivots, the first and second ends 13, 17 are brought closer together or further apart. Associated with the first and second ends 13, 17 are a first conduit 24 and second conduit 26. Though the first and second conduits 24, 26 are shown as cylinders, those skilled in the art in view of the teachings herein will appreciate that the first and second conduits, or any conduits described herein, could take any number of appropriate shapes including oval, orthogonal, triangular, etc., and may fully or partially encompass the saw component. The system 10 also includes a flexible saw component 20 that is guided within the first and second conduits 24 and 26. As best shown in FIG. 1B, the flexible saw component 20 is exposed between the distal portion of first and second conduits 24, 26. As used herein, the term "proximal" refers to a location that would be closer to the user and the term "distal" refers to a location that would be closer to the donor during operation of a system.

To optimize the travel path for the cutting member, while having motion parallel to coronal plane, the portions of the saw component 20 contained within the first and second conduits 24, 26 are parallel to each other throughout a graft procurement procedure. As illustrated in FIGS. 1B and 1C, the first and second conduits 24, 26 are positioned along the contour path 33 that is preformed in a donor site. The saw component 20 reciprocates in between contour path and as a result, the bone is cut along the transverse plane. FIG. 1C shows how required thickness of the graft can be maintained if the saw component 20 is reciprocating without changing the depth of its motion. The contour path drilling/milling can be performed using orthopedic robots such as Robodoc, Acrobot, Caspar, Mako or a bone attached orthopedic robot HyBAR.

FIG. 2A shows a demonstration of the system 10 on a foam pad 29. In this demonstration, the first and second conduits 24, 26 are aluminum cylinders, and the system 10 is able to transfer reciprocating saw motion in the transverse plane to the coronal plane and harness a graft of desired thickness.

Figures 5A, 5B:
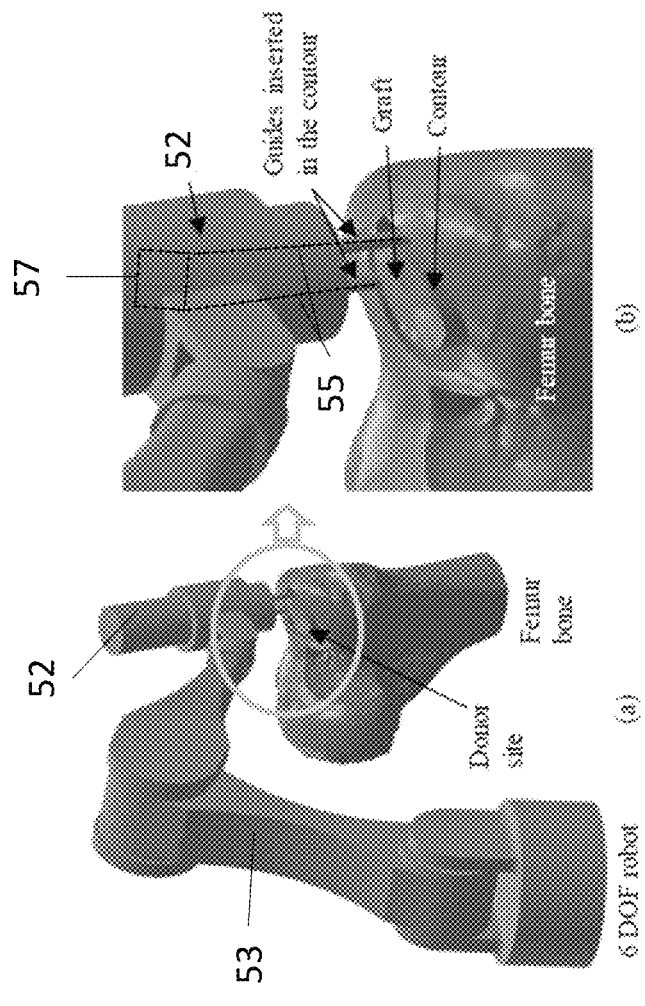
FIG. 5(A) provides an image showing a system embodiment that implements a 6-DOF robotic arm.
FIG. 5(B) provides and image showing a close up of the circled portion from FIG.
Figure 4C:
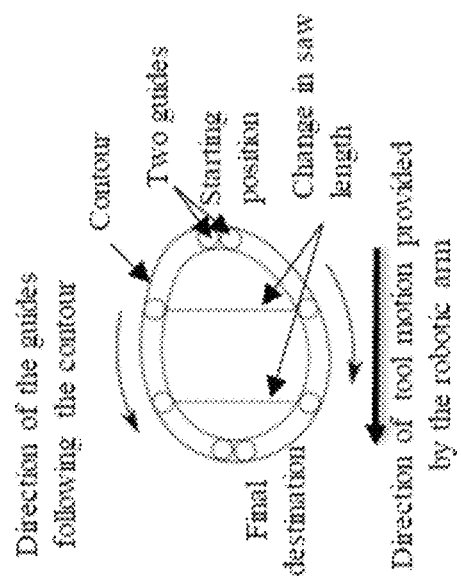
FIG. 4(C) provides a diagram showing a top view of the conduits following the contour starting from its initial position to its final destination while the robotic arm is providing the tool motion for slicing the graft from its base.

Turning to FIG. 4A-C, and FIG. 5A-B, another tissue cutting system embodiment 50 is disclosed that implements a 6 degree of freedom (DOF) robotic arm 53, first and second conduits 54, 56 and a saw component 55 that work together for extracting a tissue graft. During a graft procurement procedure, a contour 33 is first prepared around the desired donor site typically by using a drilling tool mounted on the robotic arm with the assistance of a surgeon. The conduits 54,56 are secured to a harness device 52 that is held and maneuvered by the robotic arm 53 as is shown in FIG. 5A-B. As shown in FIG. 4C, the harness device 52 is able to move the first and second conduits 54, 56 apart or together and the robotic arm 53 is able to move the harness device 52 from one end of the graft site to the other end. The harness device 52 is also equipped with an actuator 57 that is associated with the saw component 55 that applies movement (typically oscillating movement) of the saw component 55 for cutting the tissue. The robotic arm 53 provides for the gross positioning to the harness device 52 in terms of depth control and a planar motion for slicing the graft. The first and second conduits 54, 56 are capable of sliding through the contour 33 by changing the linear distance between them and the harness device 52 adjusts the saw component 55 length accordingly. With the combination of the robotic arm motion and varying the distance between the first and second conduits, it is possible to follow a desired profile and slice off a custom sized graft from its base.

Figure 6:
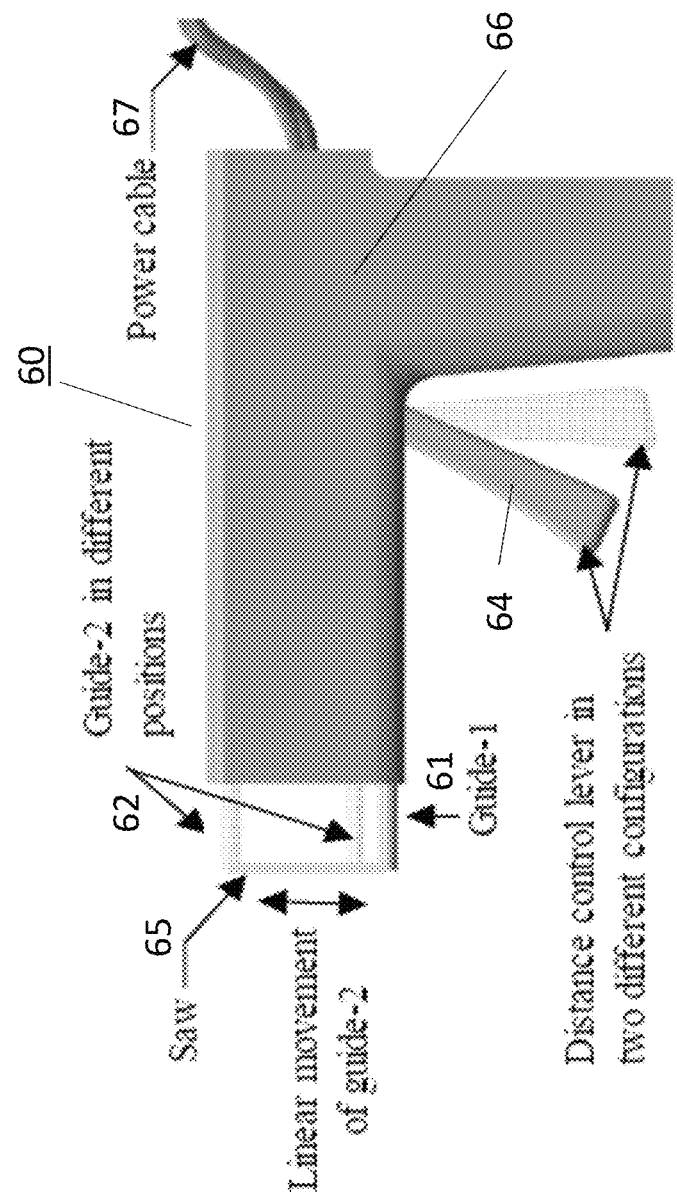
FIG. 6 provides a side view of a tissue harvesting system embodiment.

Turning to FIGS. 6-8, a tissue harvesting system 60 is shown that includes at least two conduits: one fixed conduit (guide-1) 61 and a movable conduit (guide-2) 62 held by a harness device 66. The movable conduit 62 can move linearly. The distance control lever 64 is capable of controlling the linear movement of moveable conduit (guide-2) 62 by gradually closing or opening it, so, when the lever 64 is furthest apart, the conduits 61, 62 are furthest apart with each other and vice versa. The system 60 also includes a saw component 65 and an optional power cable 67 to power the system 60.

Figure 7B:
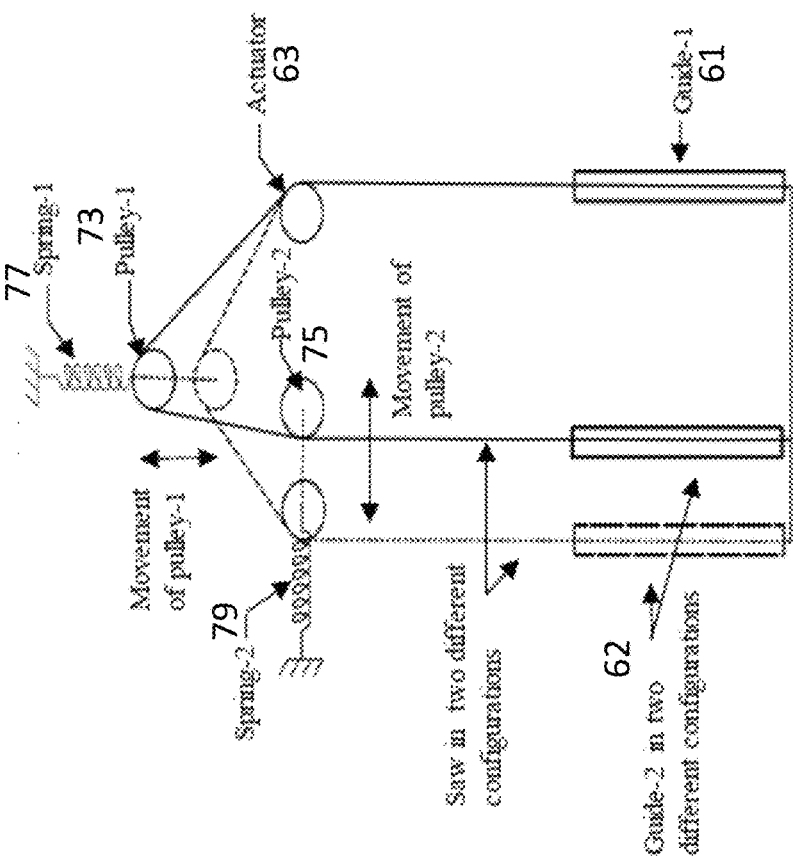
FIG. 7B provides a diagram depicting the operation components for adjusting saw length and actuation contained with the system shown in FIG. 6.
Figure 7A:
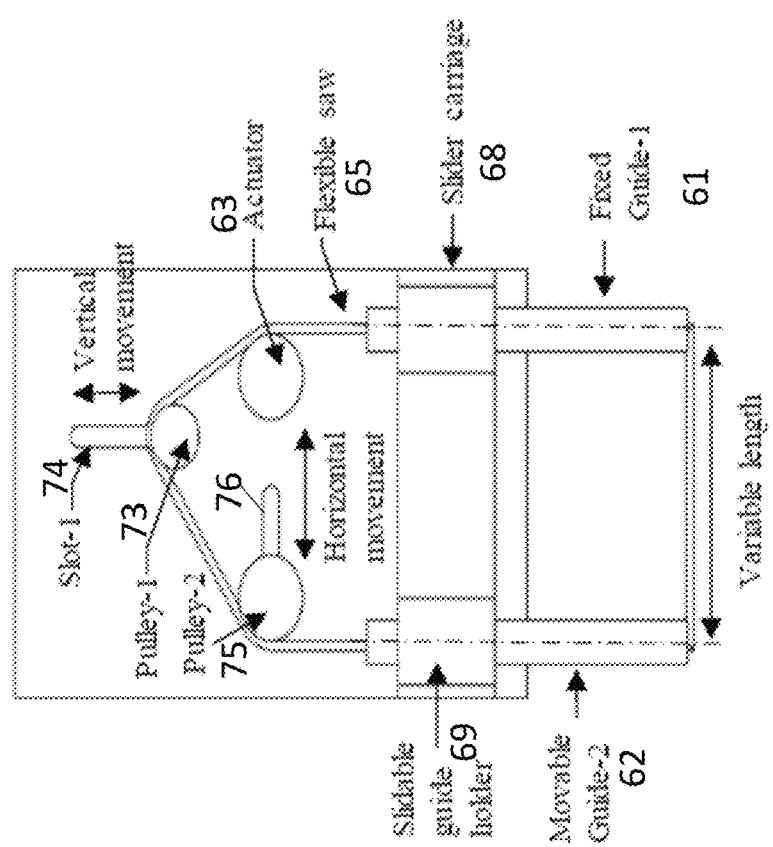
FIG. 7A provides a diagram depicting the operation components for adjusting saw length and actuation contained with the system shown in FIG. 6.

Since the conduits 61, 62 need to linearly move closer or further apart while the saw component 65 is rotating or oscillating to slice through any profile, the system 60 typically employs a saw component 65 with a variable length between the distal ends of the conduits 61,62. FIGS. 7A and 7B show the internal mechanism of the system 60 that shows how a variable length saw can be actuated by actuator 63 and controlled while the conduits moves linearly along the slider carriage 68 through slidable conduit holders 69. The saw component 65 is actuated using a high-speed motor 70. To keep the saw in the loop and provide proper tension with the actuator, two idler pulleys (pulley-1, 73 and pulley-2, 75) are implemented. These idler pulleys 73, 75 are placed in two vertical and horizontal slots 74, 76, respectively, so that the pulleys 73, 75 will slide along the slot 74, 76 to accommodate the change of length of the flexible saw when the distance control lever 64 is operated. As shown in FIG. 7A, these slots 74, 76 and idler pulleys 73, 75 also ensure that the saw component 65 is always vertical with the contact point of the idler pulley 73, 75 to transmit the force and motion most effectively. As shown in FIG. 7B, tension springs (spring-1, 77 and spring-2, 79) are used to keep the idler pulleys 73, 75 in appropriate tension with the saw component 65. FIG. 7B shows how a combination of the springs 77, 79, pulleys 73, 75 and the slots 74, 76 are able to adjust to the length of the flexible saw. The slot lengths should accommodate the maximum length change of the two conduits 61, 62.

To operate the system 60, a surgeon will insert the conduits 61, 62 inside the contour 33 such that the conduits 61, 62 are in the closest position to each other as shown in FIG. 8 and will keep conduit 61 fixed in a particular position of the contour 33 throughout the sawing operation and use that as the rotating axis to move the movable conduit 62 along the contour 33. Using the lever 64, one can control the movable conduit 62 to travel through the contour 33. Keeping one conduit fixed and changing the position of the other provides the operator with the advantage of exerting more sawing power since s/he can create a torque about the axis of the fixed conduit.

The systems described above and shown in the Figures serve to enhance current surgical techniques for osteochondral injuries and PTOA surgical treatments. This system embodiments can be used for extracting hard tissue grafts of virtually any shape and size. The technology could enable precision hard tissue harvesting in various surgical procedures that are not available currently.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

The invention claimed is:

1. A system comprising:
   a robotic arm;
   a harness device engaged with the robotic arm;
   a first conduit and a second conduit movably associated with the harness device such that the harness device moves or allows movement of the first and second conduits toward or away from each other; and
   a saw component extending within the first and second conduits and engaged with the harness device such that the harness device provides motion to the saw component to induce a cutting effect between distal ends of the first and second conduits.

2. The system of claim 1, wherein the harness device comprises an actuator that interacts with the saw component for providing motion to the saw component.

3. A method for harvesting a tissue graft using the system of claim 2, the method comprising
   providing a contour at a donor site;
   inserting the first and second conduits into a first location of the contour; and
   actuating the saw component, while moving the first and second conduits from the first location to a second location in the contour such that a tissue graft is cut at the donor site along a plane that is transverse to a plane of the contour.

4. The method of claim 3, wherein cutting at the donor site produces a flat cut surface on the tissue graft.

5. A system comprising:
   a harness device;
   a fixed conduit and a movable conduit engaged with the harness device such that a distance between the fixed conduit and movable conduit may be increased or decreased by movement of the movable conduit;
   a lever engaged with the harness device that controls the distance between the fixed conduit and movable conduit; and
   a saw component extending within the fixed conduit and movable conduit and engaged with the harness device such that the harness device provides motion to the saw component to induce a cutting effect between distal ends of the fixed and movable conduits.

6. The system of claim 5, wherein the harness device comprises an actuator that interacts with the saw component for providing motion to the saw component.

7. The system of claim 6, further comprising comprises a motor and a power source for driving the actuator.

8. The system of claim 5, further comprising comprises a first pulley and a second pulley positioned at a first slot and a second slot, respectively, defined in the harness device such that the first and second pulleys slide along the first and second slots to accommodate a change of length of the saw component brought about by a change in the distance between the fixed and movable conduits.

9. The system of claim 8, further comprising a first spring and second spring associated with the first and second pulleys, respectively, so as to maintain tension on the saw component as the length of the saw component changes.

10. A method for harvesting a tissue graft using the system of claim 5, the method comprising providing a contour at a donor site;

inserting the fixed and movable conduits into a first location of the contour; and actuating the saw component; and while the saw component is actuated, moving the fixed and movable conduits from the first location to a second location in the contour such that a tissue graft is cut at the donor site along a plane that is transverse to a plane of the contour.

11. The method of claim 10, wherein cutting at the donor site produces a flat cut surface on the tissue graft.

12. The method of claim 10, wherein the lever component adjusts the distance between the fixed and movable conduits during the moving step.

\* \* \* \* \*